United States Patent [19]

Parker et al.

[11] Patent Number: 5,684,135
[45] Date of Patent: Nov. 4, 1997

[54] CONJUGATE COMPOUNDS CONTAINING AZA-MACRO-CYCLES AND PROCESSES FOR THEIR PREPARATION

[75] Inventors: David Parker, Durham; Nigel Robert Arnold Beeley, Thame; Thomas Andrew Millican, Maidenhead, all of United Kingdom

[73] Assignee: Celltech Therapeutics Limited, Berkshire, Great Britain

[21] Appl. No.: 451,306

[22] Filed: May 26, 1995

Related U.S. Application Data

[63] Continuation of Ser. No. 178,460, Jan. 6, 1994, abandoned, which is a continuation of Ser. No. 793,373, filed as PCT/GB91/00613, Apr. 18, 1991, abandoned.

[30] Foreign Application Priority Data

Apr. 18, 1990 [GB] United Kingdom ............. 9008724

[51] Int. Cl.$^6$ .................................................. C07K 17/06
[52] U.S. Cl. .............. 530/391.1; 530/350; 530/391.3; 530/391.5; 530/391.9; 530/402; 540/465; 540/474
[58] Field of Search ...................... 530/324, 325, 530/326, 327, 328, 329, 330, 331, 350, 345, 391.1, 391.5, 391.3, 391.9, 402; 540/465, 474

[56] References Cited

U.S. PATENT DOCUMENTS

| | | | |
|---|---|---|---|
| 4,174,319 | 11/1979 | Kobuke | 260/239 |
| 4,174,428 | 11/1979 | Tabushi et al. | 540/474 |
| 4,432,907 | 2/1984 | Wieder et al. | 436/500 |
| 4,472,509 | 9/1984 | Gansow et al. | 436/548 |
| 4,659,839 | 4/1987 | Nicolotti et al. | 548/546 |
| 4,671,958 | 6/1987 | Rodwell et al. | 514/2 |
| 4,678,667 | 7/1987 | Meares | 424/85 |
| 4,877,600 | 10/1989 | Bonnemain et al. | 257/2 |
| 4,885,363 | 12/1989 | Tweedle et al. | 540/465 |
| 5,045,451 | 9/1991 | Uhr et al. | 435/7.23 |
| 5,049,667 | 9/1991 | Schaefer et al. | 540/474 |
| 5,053,503 | 10/1991 | Dean et al. | 540/474 |

FOREIGN PATENT DOCUMENTS

| | | |
|---|---|---|
| 76217/87 | 2/1988 | Australia . |
| 0173629 | 3/1986 | European Pat. Off. . |
| 0188256 | 7/1986 | European Pat. Off. . |
| 0232751 | 8/1987 | European Pat. Off. . |
| 0255471 | 2/1988 | European Pat. Off. . |
| 0382582 | 8/1990 | European Pat. Off. . |
| 0404605 | 12/1990 | European Pat. Off. . |
| 88/08422 | 11/1988 | WIPO . |
| 89/01476 | 2/1989 | WIPO . |
| WO01475 | 2/1989 | WIPO . |

OTHER PUBLICATIONS

Moi, C.F., et al., *J. Am. Chem. Soc.*, 110, 6266 (1988).
Khaw et al., *Science*. 209, 295 (1980).
Krejcarek et al., *Biochem. Biophys. Res. Comm.*, 77, 581 (1977).
Childs, R.L. and Hnatowich, D.J., *J. Nuc. Med.* 26, 293 (1985).
Stetter, H., et al., *Angew. Chem. Int. Ed. Engl.*, 15, 686 (1976).
Loncin, J.F., et al., *Inorg. Chem.*, 25, 2646 (1986).
Tweedle, M.F., et al., *J. Nuc. Med.*, 28, 705 (1988).
Goodwin, C.H., et al., *J. Nuc. Med.*, 27, 959 (1986).
Paik, C.H., et al., *J. Nuc. Med.*, 28, 572 (1987).
Paik, C.H., et al., *J. Nuc. Med.*, 29, 889 (1988).
Haseman, C.F., et al., *Eur. J. Nuc. Med.*, 12, 455 (1986).
Parker et al., *Pure & Appl. Chem.*, vol. 61, No. 9, 1637–1641 (1989).
Craig et al., *J. Chem. Soc. Chem. Commun.* (1989), pp. 794–796.
Cox et al., *J. Chem. Soc. Chem. Commun.* (1989), pp. 797–798.
Paik et al., *J. Nucl. Sci.*, vol. 30, No. 10, p. 1693–1701 (Nov./1989).
Paik et al., *Nucl. Med. Biol.*, vol. 16, No. 5, pp. 475–481 (1989).
Deshpande et al., *Nucl. Med. Biol.*, vol. 16, No. 6, pp. 587–597 (1989).

(List continued on next page.)

*Primary Examiner*—Christina Y. Chan
*Assistant Examiner*—Padmashri Ponnaluri
*Attorney, Agent, or Firm*—Mathews, Woodbridge & Collins

[57] ABSTRACT

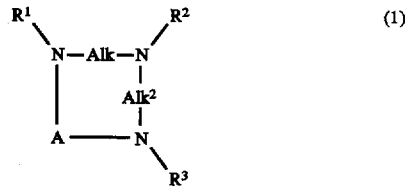

Conjugate compounds are described comprising a compound of formula (1), wherein A is a group —Alk$^3$— or —Alk$^3$N(R$^4$)Alk$^1$—, Alk$^2$, Alk$^3$ and Alk$^4$ which may be the same or different is each a $C_{1-4}$alkylene chain optionally substituted by one or more $C_{1-6}$alkyl groups; and R$^1$, R$^2$, R$^3$ and R$^4$, which may be the same or different, is each a hydrogen atom or a group—AlkR$^5$ where Alk is an optionally substituted straight or branched $C_{1-6}$ alkyl group and R$^5$ is a hydrogen atom or a —CO$_2$H, —CONR$^6$R$^7$ (where R$^6$ and R$^7$, which may be the same or different is each a hydrogen atom or an alkyl group) or —P(X$^1$)(X$^2$R$^8$)L group where X$^1$ and X$^2$ is each an oxygen or sulphur atom. R$^8$ is a hydrogen atom or an alkyl group and L is an aliphatic, aromatic, or heteroaromatic group or a linker group with the proviso that at least one of R$^1$, R$^2$, R$^3$ and R$^4$ is a group AlkP(X$^1$)(X$^2$R$^8$)L where L is a linker group; and a metal complexes and/or salts thereof, coupled to a protein, peptide or carbohydrate. The conjugates are useful for imaging and in the treatment of abnormal cell disorders, such as in the treatment of tumours.

9 Claims, No Drawings

OTHER PUBLICATIONS

Deshpande et al., *The Journal of Nuclear Medicine.* "*Copper–67–Labeled Monoclonal Antibody Lym–1, A Potential Radio–pharmaceutical for Cancer Therapy: Labeling and Biodistribution in RAJI Tumored Mice*", vol. 29, No. 2, pp. 217–225 (Feb. 1988).

Franz, J., et al., Abstract from Journal of Nuclear Medicine, Abstract No. 553, vol. 26, No. 5 (May 1985).

Meares, Claude F., Protein Tailoring for Food and Medicine Uses edited by R.E. Feeny et al., *Attaching Metal Ions to Antibodies*, pp. 339–352 (1986).

Goodwin, D.A., et al., Abstract of "In Complex of a New Macrocyclic Bifunctional Chelator TETA", presented at European Nuclear Medicine Congress Meeting at Barbican, London, No. 113 Sep. 3–6 (1985).

Meares et al., Int. J. Cancer Suppl., 2, 99–102 (1988).

Meares et al., Br. J. Cancer, 62, 21–26 (1990).

Gransow et al., ACS Symposium Series, No. 241, "Generator Produced Bi–212"(1984).

Moi et al., *Anal. Biochem.*, 148, 249–253 (1985).

Broan et al., J. Chem. Soc. Chem. Commun. pp. 1739–1741 (Dec. 1, 1990).

Broan et al., J. Chem Soc Chem Commun pp. 1738–1739 (Dec. 1, 1990).

Kabachnik et al., Bull Acad Sci USSR DIV Chem Sci vol. 33, No. 4, Part I, pp. 769–777 (1984).

Kabachnik et al., Bull Acad Sci USSR DIV Chem Sci vol. 33, No. 4, pp. 777–782 (1984).

Yatsimirrskii et al., Chem. Abstr. vol. 100, No. 198535c 1984.

CONJUGATE COMPOUNDS CONTAINING AZA-MACRO-CYCLES AND PROCESSES FOR THEIR PREPARATION

CROSS-REFERENCE TO RELATED APPLICATIONS

This is a continuation of Ser. No. 08/178,460, filed Jan. 6, 1994, now abandoned, which is a continuation of Ser. No. 07/793,373 filed as PCT/GB91/00613, Apr. 18, 1991, now abandoned.

FIELD OF THE INVENTION

This invention relates to conjugate compounds containing the functionalised aza macrocycles and metal complexes thereof to processes for their preparation, and to their use in diagnosis and therapy.

BACKGROUND TO THE INVENTION

The attachment of metal ions to proteins, peptides and other, smaller molecules is a fast expanding technology, which has numerous proven and potential applications in research, in industry and, particularly, in medicine.

In recent years, much of the impetus behind the development of this technology has been the ability to link metal ions to antibodies, especially monoclonal antibodies. Such metal labelled antibodies have found a widespread use, especially in medicine, where they have been employed, for example, to target the metal ion to a specific tissue type, both in vitro and in vivo. Thus, metal labelled antibodies have applications in locating specific tissue types (e.g. employing computer-aided tomographic techniques where the metal ion is in some way detectable) and in the treatment of cell disorders (e.g. treating mammalian tumours where the metal ion is a cytotoxic radionuclide).

Conventionally, attachment of the metal ion to a protein such as an antibody has been achieved by complexation by an acyclic chelate such as a substituted diethylenetriamine-pentaacetic acid [Gansow O. A. et al Inorg. Chem., (1986), 25, 2772] or ethylenediaminetetraacetic acid [Meares C. F. et al. Acc. Chem. Res., (1984), 17, 202] covalently linked to the antibody. Such acylic complexes however tend to be unstable in vivo either as a result of acid-catalysed decomplexation or competitive chelate binding by $Ca^{3+}$ or $Zn^{2+}$ in serum, or as a result of competition from transferrin [Moerlein, S. M. et al, Int. J. Nuc. Med. Biol., (1981) 8, 277]. The lack of stability can result in uncomplexed metal atoms in the body which have a cytotoxic effect on healthy tissue (e.g. bone marrow) or which markedly reduce the signal-to-noise ratio of an imaging technique.

A possible alternative to the use of acyclic chelates in the labelling of antibodies in the use of macrocyclic ligands, which has been suggested by a number of workers [Gansow O. A. et al. Am. Chem. Soc. Symp. Ser., (1984, 241, 215; UK Patent specification Publication No. 2122641; International Patent Specifications Nos. WO89/01475 and WO89/01476 and European Patent Specification No. 305320; and Moi M. K. et al, Anal. Biochem., (1985), 148, 249–253].

We have now found a new class of functionalised aza macrocycles, members of which are able to form kinetically inert complexes with metal ions. The macrocycles are particularly useful for attachment to proteins, especially antibodies, to provide conjugate compounds capable of binding metals with good association rates to give complexes which are advantageously stable in vivo and which possess an advantageous biodistribution profile.

Thus, according to one aspect of the present invention we provide a conjugate compound comprising a compound of general formula (1):

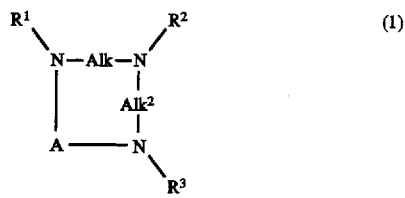

wherein

A is a group —$Alk^3$— or —$Alk^3N(R^4)Alk^4$—;

$Alk^1$, $Alk^2$, $Alk^3$ and $Alk^4$ which may be the same or different is each a $C_{1-4}$alkylene chain optionally substituted by one or more $C_{1-6}$alkyl groups; and $R^1$, $R^2$, $R^3$ and $R^4$, which may be the same or different, is each a hydrogen atom or a group —$AlkR^5$ where Alk is an optionally substituted straight or branched $C_{1-6}$ alkyl group and $R^5$ is a hydrogen atom or a —$CO_2H$, —$CONR^6R^7$ (where $R^6$ and $R^7$, which may be the same or different is each a hydrogen atom or an alkyl group) or —$P(X^1)(X^2R^8)L$ group where $X^1$ and $X^2$ is each an oxygen or sulphur atom. $R^8$ is a hydrogen atom or an alkyl group and L is an aliphatic, aromatic, or heteroaromatic group or a linker group with the proviso that at least one of $R^1$, $R^2$, $R^3$ and $R^4$ is a group $AlkP(X^1)(X^2R^8)L$ where L is a linker group; and protected derivatives and metal complexes and/or salts thereof, coupled to a protein, peptide or carbohydrate.

It will be appreciated that formula (1) [and, where appropriate, the following formulae herein], is intended to cover all stereoisomers of the compounds concerned, including mixtures thereof.

The compound of formula (1) may be coupled through any thiol, amino, carboxyl, hydroxyl, aldehyde, aromatic or heteroaromatic group present in the protein, peptide or carbohydrate.

In a preferred aspect of the invention, we provide a conjugate compound which comprises a compound of formula (1) or a metal complex and/or salt thereof, coupled to an antibody.

It is to be understood that conjugate compounds according to the invention may contain more than one molecule of a compound of formula (1) coupled to any one protein, peptide or carbohydrate molecule.

$Alk^1$, $Alk^2$, $Alk^3$ and $Alk^4$ in the compounds of formula (1) may each be a chain —$CH_2$—, —$(CH_2)_2$—, —$(CH_2)_3$— or —$(CH_2)_4$—, optionally substituted by one or more $C_{1-6}$ alkyl, e.g. methyl or ethyl groups. Examples of substituted alkyl groups represented by $Alk^1$, $Alk^2$, $Alk^3$ and $Alk^4$ include —$CH_2CH:CH_3$)— or —$CH_2C(CH_3)_2$—.

When the group L in compounds of formula (1) is an aliphatic group it may be for example an optionally substituted straight or branched chain alkyl, alkenyl, alkynyl, alkoxy or alkylthio group, optionally interrupted by one or more heteroatoms, or a cycloalkyl or cycloalkenyl group. When L is an aromatic group it may be for example an aryl or aralkyl group. Heteroaromatic groups represented by L include heteroaryl and heteroaralkyl groups.

Thus, for example, L may be an optionally substituted $C_{1-10}$alkyl (e.g. $C_{1-6}$ alkyl such as methyl, ethyl, n-propyl, i-propyl, n-butyl, s-butyl or t-butyl) $C_{2-10}$alkenyl (e.g. $C_{2-6}$ alkenyl such as ethene, propene, 1-butene, 2-butene, or 2-methylpropene), $C_{2-10}$alkynyl (e.g. $C_{2-6}$ alkynyl such as ethyne, propyne, 1-butyne, or 2-butyne) $C_{1-10}$alkoxy (e.g.

$C_{1-6}$alkoxy such as methoxy, ethoxy, n-propoxy, i-proproxy, n-butoxy, s-butoxy, or t-butoxy) or $C_{1-10}$alkylthio (e.g. $C_{1-6}$alkylthio such as methylthio, ethylthio, n-propylthio, i-propylthio, n-butylthio, s-butylthio, or t-butylthio) group optionally interrupted by one or more heteroatoms selected from —O—, —S— or —NR$^6$ (where R$^6$ is a hydrogen atom or a $C_{1-6}$ alkyl group), for example an alkoxyalkyl (e.g. methoxymethyl) alkylthioalkyl (e.g. methylthiomethyl) or alkoxyalkoxy or alkylthioalkoxy (e.g. methoxymethoxy or methylthiomethoxy) group; or a $C_{3-8}$ cycloalkyl (e.g. cyclopropyl, cyclobutyl, cyclopentyl, or cyclohexyl) or $C_{4-8}$ cycloalkenyl (e.g. cyclobutene, cyclopentent, cyclohexene, or cyclohexadiene) group.

When L is an aryl group it may be for example an optionally substituted $C_{6-12}$aryl group such as an optionally substituted phenyl or naphthyl group.

When L is an aralkyl group it may be for example an optionally substituted $C_{6-12}$ar$C_{1-6}$alkyl group for example a phen$C_{1-6}$alkyl group such as benzyl or phenethyl.

When L is a heteraryl group it may be for example an optionally substituted $C_{4-10}$heteroaryl group containing one or more heteroatoms selected from —O—, —NH— or —S—, for example a pyridyl, furanyl or thienyl group.

When L is a heteroaralkyl group it may be for example an optionally substituted $C_{4-10}$heteroar$C_{1-6}$alkyl group containing one or more heteroatoms selected from —O—, —NH— or —S— for example a thienyl$C_{1-6}$alkyl (e.g. thienylmethyl) or pyridyl$C_{1-6}$alkyl (e.g. pyridylmethyl) group.

Optional substituents which may be present on alkyl, alkoxy, aryl, aralkyl, heteroaryl or heteroaralkyl groups present in the group L in compounds of formula (1) include one or more halogen atoms e.g. chlorine, bromine, fluorine or iodine atoms, or one or more groups selected from hydroxyl, $C_{1-6}$ alkyl e.g. methyl or ethyl. $C_{1-6}$ alkoxy, e.g. methoxy or ethyl, $C_{1-6}$alkylthio, e.g. methylthio, amino (—NH$_2$), substituted amino, e.g. NR$^7$R$^8$ where R$^7$ is a hydrogen atom or a $C_{1-6}$alkyl group and R$^8$ is a $C_{1-6}$ alkyl group such as methylamino or dimethylamino), nitro, cyano, carboxyl, —CONR$^6$R$^7$ (e.g. —CONH$_2$), —SO$_2$NR$^6$R$^7$ (e.g. SO$_2$NH$_2$) or $C_{3-8}$cyclalkyl (e.g. cyclopropyl, cyclobutyl, cyclopentyl or cyclohexyl) groups.

In the compounds of formula (1), it will be appreciated that the nature of the linker group represented by L may be varied widely without substantially affecting the usefulness of the compounds. Thus, the linker group L may be a group of formula —L$^1$(Z)w where L$^1$ is an optionally substituted polyvalent, especially bivalent, radical of an aliphatic, aromatic, heteroaromatic or araliphatic compound, Z is the residue of a reactive functional group and w is zero or an integer 1.

When L$^1$ is an aliphatic group, it may be for example an optionally substituted aliphatic hydrocarbyl chain, optionally interrupted by one or more heteroatoms selected from —O— or —S— or by one or more —N(R$^9$)— (where R$^9$ is a hydrogen atom or a $C_{1-6}$alkyl group), —CON(R$^9$)—, —N(R$^9$)CO—, cycloaliphatic, aromatic, or heteroaromatic groups.

In the above definition, and in the same context whenever it appears below, the term "interrupted by" as applied to cycloaliphatic or aromatic groups is to be understood to also mean that these particular groups may additionally be present linked to the terminal carbon atom of the hydrocarbyl chain represented by L$^1$, at the opposite end of the chain to the carbon atom attached to the macrocycle.

Thus, for example, L$^1$ may be an optionally substituted straight or branched $C_{1-20}$alkylene, $C_{2-20}$alkenylene, or $C_{2-20}$alkylnylene chain, optionally interrupted by one or more —O— or —S— atoms or $C_{5-8}$cycloalkylene (e.g. cyclopentylene or cyclohexylene), $C_{6-12}$aromatic (e.g. phenylene or substituted phenylene), $C_{5-10}$heteroaromatic (e.g. furanyl, pyridyl), —N(R$^9$)—, —CON(R$^9$)— or —N(R$^9$)CO— groups.

When L$^1$ is an aromatic group it may be an aryl group, for example a $C_{6-12}$aryl group such as a phenyl group.

When L$^1$ is a heteroaromatic group it may be for example an optionally substituted heteroaryl or heteroaralkyl group e.g. a $C_{4-10}$heteroaryl or $C_{4-10}$heteroar $C_{1-6}$alkyl group containing one or more heteroatoms selected from —O—, —NH— or —S—, for example a pyridyl, pyridyl$C_{1-6}$alkyl, e.g. pyridylmethyl, furanyl, furanyl$C_{1-6}$alkyl, e.g. furanylmethyl, thienyl or thienyl$C_{1-6}$alkyl, e.g. thienylmethyl.

Examples of substituents which may be present on the group L$^1$ include one or more halogen atoms, e.g. fluorine, chlorine, bromine, or iodine atoms or one or more groups selected from $C_{1-6}$ alkyl (e.g. methyl or ethyl), $C_{1-6}$alkoxy (e.g. methoxy or ethoxy), $C_{1-6}$alkylthio e.g. methylthio, hydroxy, nitro, —N(R$^{10}$)(R$^{11}$), [where R$^{10}$ is a hydrogen atom or a $C_{1-6}$alkyl group and R$^{11}$ is a $C_{1-6}$alkyl group; e.g. —NHCH$_3$ or —N(CH$_3$)$_2$], or substituted amido, e.g. a group of formula —(CH$_2$)$_d$CON(R$^{12}$)(R$^{13}$) [where d is zero or an integer 1 to 4 inclusive, R$^{12}$ is a hydrogen atom or a $C_{1-6}$alkyl group, e.g. methyl and R$^{13}$ is an optionally substituted $C_{1-6}$alkyl group].

Substituted alkyl groups represented by R$^{13}$ include for example $C_{1-6}$alkyl groups substituted by one or more halogen atoms, or nitro, amino or hydroxy groups.

The residue of a reactive functional group represented by Z may in general by the residue of any group capable of reacting with a thiol, amino, carboxyl, hydroxyl, aldehyde, aromatic or heteroaromatic group. Aromatic groups include, for example, phenolic groups. Heteroaromatic groups include for example imidazolyl groups.

In particular, Z may be for example —S—, —NH—, —NHN=, —N(CH$_3$)N=, —NHCONHN=, —NHCSNHN=, —N(Ph)N=, (where Ph is optionally substituted phenyl), —NC(O)—, —NC(S)—, —CO—, a vinyl group of formula —Het$^1$— C(Het$^2$)CH$_2$ (where Het$^1$ and Het$^2$, which may be the same or different, is each a nitrogen containing heterocyclic group, e.g. a pyridyl group or Het$^1$ is a nitrogen containing heterocyclic group and Het$^2$ is a hydrogen atom), for example a vinyl pyridyl group of formula

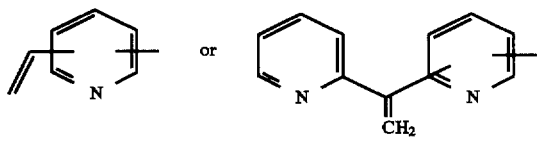

especially

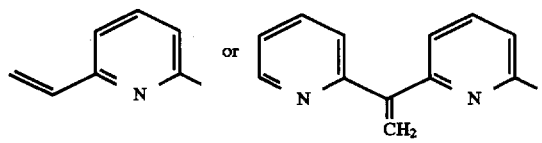

an imide, or a dione of formula

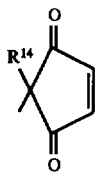

(where $R^{14}$ is a $C_{1-4}$alkyl e.g. methyl group).

In the compounds of formula (1) alkyl groups represented by $R^6$, $R^7$ or $R^8$ may be straight or branched chain groups and may be for example $C_{1-6}$ alkyl groups such as methyl or ethyl groups.

The group $CONR^6R^7$ when present in compounds of formula (1) may be for example —$CONH_2$, —$CONHCH_3$, —$CON(CH_3)_2$, —$CONHCH_2CH_3$ or —$CON(CH_2CH_3)_2$.

Alk in the compounds of formula (1) may be for example a methyl, ethyl, n-propyl, i-propyl, n-butyl, s-butyl or t-butyl group. Such groups may be substituted, for example, by one or more halogen atoms, e.g. fluorine or chlorine atoms.

Metal complexes of the compounds of formula (1) in which A is —$Alk^3N(R^4)Alk^4$— include complexes wherein the metal is di- or tripositive and has a coordination number 6 or greater, especially 8. Examples of such metals include manganese (Mn), iron (Fe), indium (In), copper (Cu), lead (Pb), bismuth (Bi), yttrium (Y), terbium (Tb), gallium (Ga), gadolinium (Gd), scandium (Sc), other transition metals with atomic numbers 21–29, 42, 43, 44 or 75, and other lanthanides with atomic numbers 57–70. In, Y, Ga, Tb, Gd, and Sc are preferred particularly In, Y, Gd, and Ga. The metal may be a radioactive isotope, for example $^{90}Y$.

Metal complexes of the compounds of formula (1) in which A is —$Alk^3$— include complexes wherein the metal is di- or tri-positive and has a coordination number from 2 up to 6, especially 6. Examples of such metal(s) include indium (In) copper (Cu), lead (Pb), bismuth (Bi), colbalt (Co), gadolinium (Gd) and gallium (Ga), In, Ga, Gd, Co and Cu are preferred, particularly In, Gd and Ga. In general the metal is preferably a radioactive isotope. Indium, especially $^{111}$In, is particularly preferred.

In general, optimum binding of the metal to the compounds of formula (1) may be achieved by selection of the ring size and where appropriate by adjusting the potential coordination number by choice of the group $R^1$, $R^2$, $R^3$ or $R^4$.

Salts of the compounds of formula (1) or metal complexes thereof include salts with inorganic or organic bases, for example alkali metal or alkaline earth metal salts such as lithium, sodium, potassium, magnesium or calcium salts; amine salts such as those from primary, secondary or tertiary amines; for example ethanolamine, diethanolamine, morpholine, glucamine, N-methylglucamine, or N,N-dimethylglucamine salts and amino acid salts such as lysine, argine and ornithine salts. Pharmaceutically acceptable salts are particularly preferred.

A particularly useful group of conjugate compounds according to the invention is that wherein the compound of formula (1) A is —$Alk^3$— or —$Alk^3N(R^4)Alk^4$— and $Alk^1$, $Alk^2$, $Alk^3$ and $Alk^4$ is each a chain —$(CH_2)_2$—.

One group of compounds of formula (1) has the formula (1a):

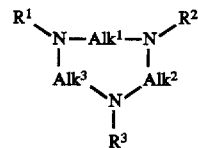

where $R^1$, $R^2$, $R^3$, $Alk^1$, $Alk^2$ and $Alk^3$ are as defined for formula (1) with the proviso that at least one of $R^1$, $R^2$ and $R^3$ is a group $AlkP(X^1)(X^2R^8)L$ where L is a linker group; and metal complexes and/or salts thereof.

Indium complexes of the compounds of formula (1a) are particularly preferred.

Particularly important compounds of formula (1a) are those of formula (1b)

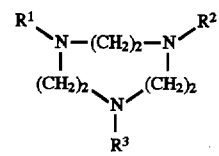

wherein $R^1$, $R^2$ and $R^3$ are as defined for formula (1a) and metal complexes and/or salts thereof.

Indium complexes of the compounds of formula (1b) are particularly preferred.

Another group of compounds of formula (1) has the formula (1c):

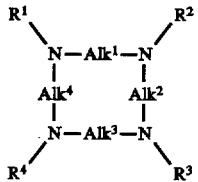

wherein $R^1$, $R^2$, $R^3$, $R^4$, $Alk^1$, $Alk^2$, $Alk^3$ and $Alk^4$ are as defined for formula (1) with the proviso that at least one of $R^1$, $R^2$, $R^3$ and $R^4$ is a group $AlkP(X^1)(X^2R^8)L$ where L is a linker group; and protected derivatives and metal complexes and/or salts thereof.

Yttrium and gadolinium complexes of the compounds of formula (1c) are particularly preferred.

An important group of compounds of formula (1c) are those of formula (1d)

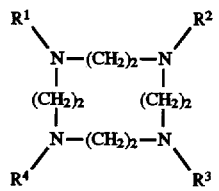

wherein $R^1$, $R^2$, $R^3$ and $R^4$ are as defined for formula (1c); and metal complexes ad/or salts thereof.

Yttrium and gadolinium complexes of the compounds of formulae (1d) are particularly preferred.

In general, in the compounds of the various formulae described above, the group $AlkP(X^1)(X^2R^8)L$ when present is preferably a group $AlkP(O)(OR^8)L$, for example a group $AlkP(O)(OH)L$, such as —$CH_2P(O)(OH)L$. Particular instances of groups of this latter type are those of formula —$CH_2P(O)(OH)L$ where L is $C_{1-6}$alkyl e.g. methyl or —$L^1$—$(Z)w$.

The groups $R^1$, $R^2$, $R^3$ and $R^4$ in the various formulae described above are preferably groups —$AlkR^5$ where Alk is an optionally substituted straight or branched $C_{1-6}$alkyl group, and is particularly a methylene group, and $R^5$ is a $CO_2H$, —$CONR^6R^7$ or —$P(X^1)(X^2R^8)L$ group, particularly a group —$P(O)(OH)L$.

The metal complexes of the conjugate compounds have a diagnostic use as imaging agents, for example as contrast agents, in vitro and in vivo. The compounds of formula (1) and the metal complexes and/or salts thereof are also cytotoxic agents and may be used in the treatment of abnormal cell disorders, for example in the treatment of tumours. For use as diagnostic and/or therapeutic agents, conjugates may be employed using conventional methods, (e.g. for formulation and presentation) already in use for metal complexing agents.

Particularly useful conjugate compounds according to the invention are those comprising a compound of formula (1b) or formula (1d) or a metal complex and/or salt thereof, coupled to an antibody. The indium, yttrium and gadolinium complexes of these conjugates are especially important.

The antibody in conjugates according to the invention may in general belong to any immunoglobulin class. Thus for example it may be an immunoglobulin M antibody or, in particular, an immunoglobulin G antibody. The antibody molecule may be of animal, for example mammalian origin, and may be for example of murine, rat or human origin. It may be a natural antibody or a fragment thereof, or, if desired, a recombinant antibody or antibody fragment i.e. an antibody molecule or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework region of a second, different antibody (as described in European Patent Specification No. 239400); (2) recombinant antibodies or fragments wherein non-Fv sequences have been substituted by non-Fv sequences from other, different antibodies (as described in European Patent Specification Nos. 171496, 173494 and 194276; or (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Applications Nos. WO89/01974 and WO89/01782 respectively).

The antibody may be of polyclonal or, preferably, monoclonal origin. It may be specific for any number of antigenic determinants, but is preferably specific for one. The antigenic determinants may be any hapten or antigenic determinant associated with any antigen. Particular antigens include those associated with animals, e.g. humans, [for example normal animal tissue or organ cell-associated antigens, tumour cell associated antigens (for example oncofetal antigens such as carcinoembryonic antigen or alphafetoprotein, placental antigens such as chorionic gonadotropin and placental alkaline phsophatase, and prostate antigens such as prostatic acid phsophatase and prostate specific antigen) and antigens associated with components of body fluids such as fibrin or platelets], viruses, bacteria and fungi.

In a preferred aspect of the antibody may be capable of recognising and binding a tumour cell-associated antigen, particularly one or more epitopes on the TAG-72 antigen associated with human breast and colon tumours. A particularly preferred antibody of this type is the monoclonal antibody B72.3 [Colcher, D. et al Proc. Nat. Acad. Sci. USA (1981), 78 3199] or a fragment thereof, particularly a $F(ab')_2$ fragment.

The antibody will in general be coupled to the remainder of the conjugate of the invention (i.e. the macrocycle and linker) through any appropriate reactive atom or group, for example a nitrogen or especially, sulphur atom, present in the antibody. It will be appreciated that any one antibody molecule may contain more than one reactive group capable of coupling with the macrocycle and linker.

The conjugate compounds of the invention may be formulated for use in accordance with conventional practice. Thus according to a further aspect of the invention we provide a composition comprising a conjugate compounds comprising a compound of formula (1) coupled to a protein, peptide or carbohydrate, or a metal complex and/or salt thereof, together with one or more pharmaceutically acceptable carriers.

Particularly suitable compositions according to the invention are those adapted for parenteral administration, especially by injection or infusion. Suitable formulations of this type include suspensions solutions or emulsions of the conjugate in oily or aqueous vehicles, and may contain formulatory agents such a suspending, stabilising and/or dispersing agents. Alternatively the conjugate may be in powder form for reconstitution with a suitable vehicle, e.g. sterile pyrogen-free water before use. If desired the conjugate may be presented in unit dosage form, and/or together with one or more active ingredients or imaging agents. Suitable formulations of this type include solutions of the conjugate according to the invention in isotonic saline.

The quantities of conjugates of the invention used in formulations according to the invention will vary according to the intended use and, in particular cell target, but may be easily determined in accordance with conventional practice for reagents of this type.

Conjugates of the invention may be prepared by the following processes wherein the groups and symbols, A, $R^1$, $R^2$, $R^3$, $R^4$, $R^5$, Alk, $Alk^1$, $Alk^2$, $Alk^3$ and $Alk^4$, are as defined for formula (1) except where stated otherwise. Where a metal complex is desired as a final product, the complexation with a metal atom may be carried out as a final step in the production process, as described below for the complexation of compounds of formulae (1), or alternatively it may be desirable to complex the metal at an earlier stage in the process, providing of course that the requisite macrocycle structure is present. In the following processes, it may be desirable to use starting materials in which functional groups in the linker group are in a protected state, or which contain a precursor of the group, as discussed below.

Metal complexes for use according to the invention may be prepared by reacting a compound of formula (1) or a salt thereof with a metal salt (e.g. a nitrate, halide, such as a chloride, acetate, carbonate or sulphate) or a metal oxide.

The reaction may be performed in an appropriate solvent, for example an aqueous or non-aqueous solvent (e.g. acetonitrile, acetone, propylene carbonate, dimethylformamide or dimethylsulphoxide) at any suitable temperature from 0° C. to 100° C. such as 10° C. to 85° C.

Salts of compounds of formula (1) may be prepared by reacting a compound of formula (1) with a base in an appropriate solvent, for example an aqueous or non-aqueous solvent as described above, at any suitable temperature from 0° C. to 100° c.

Compounds of formula (1) in which one or more of $R^1$, $R^2$, $R^3$ and $R^4$ is each a group $AlkP(X^1)X^2H)L$ may be prepared by interconversion of a corresponding compound of formula (1) in which one or more of $R^1$, $R^2$, $R^3$ and $R^4$ is each a group $AlkP(X^1)(X^2R^8)L$ [where $R^8$ is an alkyl group] by treatment with an acid, for example an inorganic acid such as hydrochloric acid at an elevated temperature, for example the reflux temperature.

Compounds of formula (1) in which $R^1$ is a group $AlkP(X^1)(X^2R^8)L$ where L is a linker group, and the remaining groups $R^2$, $R^3$ and $R^4$ is each a group $AlkP(X^1)(X^2R^8)L$ where $R^8$ is an alkyl group, may be prepared by reaction of a compound of formula (2)

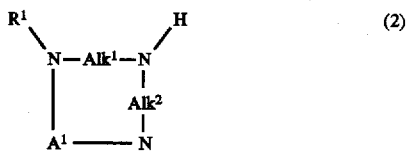

[where $R^1$ is as just defined and $A^1$ is —$Alk^3$— or $Alk^3NHAlk^4$—] with a phosphine $P(L)(X^1$—$Alk^6)(X^2R^8)$ [where $R^8$ is as just defined and $Alk^6$ is an alkyl group, for example an ethyl group] in the presence of formaldehyde, paraformaldehyde or an aldehyde RCHO (where R is a $C_{1-5}$alkyl group).

The reaction may be performed in a solvent, for example an organic solvent such as an ether, e.g. a cyclic ether such as tetrahydrofuran at an elevated temperature e.g. the reflux temperature.

Alternatively, a compound of formula (1) in which $R^1$ is a group $AlkP(X^1)(X^2R^8)L$ where L is a linker group may be prepared by reaction of compound of formula (2) with a reagent $R^5AlkD$ where D is a displaceable group such as a halogen, e.g. chlorine atom or a sulphonyloxy group, e.g. a methanesulphonyloxy group.

The reaction may be performed in a solvent such as water or an organic solvent such as a nitrile, e.g. acetonitrile, or an alcohol, e.g. ethanol, or an amide, e.g. dimethylformamide, in the presence of a base such as an alkali metal carbonate or hydroxide, e.g. sodium, potassium or caesium carbonate, or sodium, potassium or lithium hydroxide, at an elevated temperature e.g. the reflux temperature.

In this reaction, any —$CO_2H$ group present in $R^5AlkD$ may need to be protected, for example as an ester, e.g. a methyl ester. The acid may be regenerated after the desired reaction is complete, for example by hydrolysis using an acid such as sulphuric acid. Similarly, reactive functional groups in the linker group L may need to be protected. For example amine ($NH_2$) groups may be protected by acylation, for example as acetylamino or benzoylamino groups. The free amine may be regenerated from such groups by reaction with an acid such as an inorganic acid, e.g. hydrochloric acid, at an elevated temperature.

Compounds of formula (1) may also be prepared by interconversion from other compounds of formula (1). Thus one functional group Z may be exchanged for another and, if desired a linker group L changed to another by appropriate manipulative reactions. For example, a compound of formula (1) where L is a group $L^2$—NHCO—$L^3$—Z (where —$L^2$—NHCO—$L^3$ represents the group $L^1$) may be prepared by reaction of a corresponding compound wherein L represents $L^2$—$NH_2$ with a reagent $R^aO$—$L^3$—Z (where $R^a$ is for example an imide, such as succinimide, or a substituted phenyl group such as a p-nitrophenyl group) in the presence of a tertiary amine such as diisopropylethylamine or N-methylmorpholine, in a solvent such as dimethylformamide or dimethylsulphoxide.

A conjugate compound according to the invention may be prepared by reaction of a compound of formula (1) or a metal complex thereof [wherein at least one group $R^1$, $R^2$, $R^3$ or $R^4$ is a group $AlkP(X^1)(X^2R^8)L$ and L is a group $L^1$—Z] with a protein, peptide or carbohydrate in a aqueous solvent, for example an inorganic buffer such as a phosphate buffer at an appropriate temperature for example at 0° C.–40° C., e.g. 0° C.–10° C.

The protein, peptide or carbohydrate may be obtained using procedures well known in the art. If desired, before the coupling reaction, the protein, peptide or carbohydrate may first be treated to yield appropriate groups for reaction with the compound of formula (1). Thus, for example, the protein, peptide or carbohydrate may be subjected to oxidation, for example periodate oxidation to yield aldehyde groups, or may be treated with a reagent [e.g. Traut's reagent (2-iminoithiolane) using standard procedures to generate free sulphydryl groups in the molecule.

Intermediates of formula (2) may be prepared by reaction of a compound of formula (3)

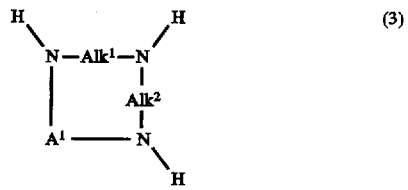

with a compound $DalkP(X^1)(X^2R^8)L$ in the presence of a base in a suitable solvent at an elevated temperature as just described for the preparation of compounds of formula (1). By varying the molar ratio of the compound of formula (2) and the compound $DalkP(X^1)(X^2R^8)L$ such that the latter is increased relative to the former, (for example from around 2:1 to 1:1 and further compounds of formula (2) containing more than $AlkP(X^1)(X^2R^8)L$ group as just defined may be prepared.

Intermediates of formula (3) and intermediates $DAlkP(X^1)(X^2R^8)L$ are either known compounds or may be prepared from known starting materials using methods analogous to those used for the preparation of the known compounds for example as described in the following Intermediates and Examples.

The following Intermediates and Example illustrate the invention. The following abbrevations are used: Ph:phenyl; Ms:$CH_3SO_2$—; Et:ethyl.

INTERMEDIATE 1

Preparation of $HOCH_2P(O)(OH)(CH_2)_3NHCOPh$

To a solution of N-benzamido allylamine (7.47 g) and hypophosphorus acid (8.66 g, 50% solution) in dioxane (100 ml) was added t-butylperoxide (0.4 g) and the mixture was heated to reflux for 18 h. Solvents were removed under reduced pressure and $^1H$ NMR analysis of the residue revealed that the olefinic resonances had disappeared. The residue was redissolved in dioxane (50 ml) and paraformaldehyde (25 g) was added and the mixture heated to reflux for 72 h. After removal of solvent the residue was chromatographed on silica (eluant 70% $CH_2Cl_2$, 25% methanol, 5% $NH_4OH$) to yield the ammonium salt of the title acid as a a pale yellow glass: δp ($D_2O$+41.1 ppm; $δ_c$ ($D_2O$) 170.04 (CONH), 134.0 ($C_6H_5$CCO); 132.28, 128.98, 127.22 (CH), 59.73 ($PCH_2OH$, d, $J_{CP}$ 99 Hz); 41.01 ($CONHCH_2$); 25.12 ($PCH_2CH_2$, d, $J_{CP}$=81 HZ); 22.03 ($PCH_2CH_2CH_2NHCO$) $δ_{H(D2O)}$ 7.79 (2H, dd, ortho ArH), 7.57 (4H mult, NHCO +ArH); 3.81 (2H, d, J=6.1 Hz, $PCH_2OH$); 3.71 (2H, t, J=6.9 Hz, $CH_2NCO$), 1.8 (4H, multi., $PCH_2CH_2$).

INTERMEDIATE 2

Preparation of $HOCH_2P(O)(OEt)(CH_2)_3NHCOPh$

To Intermediate 1 (5 g) in distilled water (50 ml) was added DOWEX® strong acid ion exchange resin (30 g, $H^+$ form) and after filtration the filtrate was evaporated under reduced pressure and the residue treated with triethylorthoformate (25 ml) and the mixture heated under argon at 90° C. for 96 h. After removal of HC(OEt)₃ under reduced pressure the residue was chromatographed on silica (CH₂Cl₂=5 to 10% methanol gradient) to yield a mixture of the desired alcohol ester and the mixed orthoformate ester. Treatment of this mixture with ethanol (50 ml, 1 ml concentrated HCl) followed by heating to reflux (36 h), evaporation and subsequent chromatographic purification as before yielded the title alcohol ester as a pale yellow oil, (4 g). m/e (d.c.i.) 286 (M⁺+1). $\delta_p$(CDCl₃)53.7 ppm $\delta_H$ (CDCl₃) 7.71 (2H, dd, ortho, CH), 7.25 (3H, mult, arom CH), 6.85 (1H, brt, NHCO), 4.05 (1H, brs OH), 3.81 (2H, dq, CH₂O), 3.70 (1H, br, d, CH₂OH); 3.31 (2H, t HNCH₂). 1.75 (4H, mult., PCH₂CH₂); 1.05 (3H, t, CH₃). $\delta_c$ (CDCl₃/CD₃CO₂D) 168.56 (CONH) 132.98 (C₅H₅CO); 131.11, 127.82, 126.58 (CH); 56.16 (PCH₂OH, d, $J_{CP}$=109 Hz); 48.53 (OCH₂CH₃); 39.62 (CONHCH₂); 21.64 (PCH₂, d, $J_{CP}$=90 Hz); 20.33 (CH₂); 15.37 (CH₃).

INTERMEDIATE 3

Preparation of MsOCH₂P(O)(OEt)(CH₂)₃NHCOPh

To a suspension of Intermediate 2 (0.57 g) in dry tetrahydrofuran (50 ml) at 0° C. was added triethylamine (1 g) and methanesulphonyl chloride (1.14 g) under argon. After 2 h stirring, ethanol (5 ml) was added and the mixture stirred for 20 min at 0° C. solvent removed under reduced pressure, and the residue taken up in ethyl acetate (30 ml), filtered and evaporated to give a residue which was chromatographed on silica gel (eluant 2 to 5% methanol in CH₂Cl₂) to yield the title mesylate as a colourless oil (390 mg) m/e (δ.c.i, CH₂Cl₂) 364 (M⁺+1). δp (CDCl₃) 45.96 ppm. $\delta_c$ (CDCl₃) 168.6 (NHCO); 134.0 (CH₅H₅CCO); 131.4, 128.4, 129.3 (CH); 62.2 (POCH₂), 61.2 (PCH₂OMs, d, $J_{PC}$=70 Hz); 39.62 (CONHCH₂), 37.6 (OSO₂CH₃); 24.0 (PCH₂CH₂, d, $J_{PC}$=100 Hz); 21.2 (CH₂), 15.4 (CH₃)

INTERMEDIATE 4

Preparation of a compound of formula (1d) where R¹ is —CH₂P(O)(OEt)(CH₂)₃NHCOPh and R², R³ and R⁴ is each —H To a solution of 1, 4, 7, 10-tetrazacyclododecane (0.16 g) in dry dimethylformamide (25 ml) was added potassium carbonate (0.13 g) at 60° C. and a solution of Intermediate 3 (0.167 g) in dimethylformamide (15 ml) over a period of 2 h under N₂. After 64 h, hplc analysis (CM300) revealed that reaction was not progressing and solvent was removed under reduced pressure. The crude residue was redissolved in dichloromethane (30 ml), filtered and evaporated before purification on a CM-300 column to yield the title monoalkylated amine (0.05 g) as a pale yellow oil. $R_t$=8.2 min (CM300 hplc): $\delta_H$ (CDCl₃) 1.30 (3H, t, J=76 Hz, OCH₂CH₃), 1.97 (5H, mult, CH₂CH₂N+NH), 2.64–2.94 (20H, mult, CH₂P), 3.55 (2H, dt, CONHCH₂) 4.06 (2H, dq, OCH₂), 7.38–7.47 (3H, mult, aryl CH), 7.93 (2H, dd, orthoCH), 8.55 (1H, t, CONH), m/e (c.i.) 440 (M⁺+1) 394(M⁺—OC₂H₅)

INTERMEDIATE 5

(a) Preparation of a compound of formula (1d) where R¹ is —CH₂P(O)(OEt)(CH₂)₃NHCOPh and R², R³, and R⁴ is each —CH₂P(O)(OEt)CH₃

To a solution of Intermediate 4 (0.015 g) in dry dimethylformamide (1 ml) was added potassium carbonate (16 mg) and MsOCH₂P(OEt)₂CH₃ (25 mg) under N₂. After heating to 80° C. for 16 h, t.l.c. (Al₂O₃) and hplc analysis (CM300) indicated no further reaction had occurred. After removal of solvent under reduced pressure, the residue was treated with dischloromethane (10 ml) filtered and evaporated to yield a residue which was purified by chromatography on alumina (eluant 0 to 2% methanol in CH₂Cl₂) to give the title tetraester as a colourless oil (11 mg). $R_t$ (CM300, hplc) 4.6 min. $\delta_H$ (CDCl₃) 1.30 (12H, t, J=7.2, CH₃CH₂), 1.49 (9H, d+d+d, PC₃), 1.80–3.70 (30H, mult., br., CH₂N+CH₂P+CH₂C) 4.05 (8H, dq, OCH₂), 7.39 (3H, mult, arylCH), 7.92 (2H, dd, ortho CH), 8.35 (1H, br, NHCO), m/e (c.i.) 800 (M⁺+1).

(b) Preparation of a compound of formula (1d) where R¹ is —CH₂P(O)(OH)(CH₂)₃NH₂ and R², R³ and R⁴ is each —CH₂P(O)(OH)CH₃

Hydrolysis of the tetraester of Part (a) (6M hydrochloric acid, 110° C., 48 h) afforded after removal of solvent the title amino-tetraacid $\delta_H$(CDCl₃) 1.35 (9H, d), 1.55–1.85 (4H, m). 2.6–3.7 (30H, m), 7.35 (2H, d), 8.35 (2H, d).

INTERMEDIATE 6

Preparation of a compound of formula (1d) where R¹ is

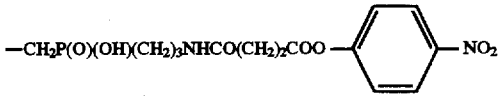

and R², R³ and R⁴ is each —CH₂P(O)(OH)CH₃

Intermediate 5(b) [27.5 mg] was dissolved in dimethylsulphoxide (1 ml) with slight heating. N-Methylmorpholine (35 µl) was added and the dimethylsulphoxide solution went cloudly and precipitation occurred. Immediately the di-4-nitrophenyl ester of succinic acid (25 mg) in dimethylsulphoxide (1.0 ml) was added and the reaction mixture heated to 150° C. for approximately 1 minute, and then left for a further 90 minutes at 45° C. The reaction mixture was purified by HPLC DYNAMAX®—Prog MAX4) to yield, after evaporation of solvent under reduced pressure, the title compound as a white powder (10 mg), m/e (FAB) 805 (M⁺+1). $\delta_H$(CDCl₃) 1.28 (9H, d), 1.5–1.8 (4H, m), 2.75–3.6 (26H, m).

INTERMEDIATE 7

Preparation of a compound of formula (1b) where R¹ is —CH₂P(O)(OEt)(CH₃)₃NHCOPh and R²and R³ is each —H Potassium carbonate (0.038 g, 0.28 mmol) was added to a solution of 1,4,7-triazocyclononane (1) (0.071 g, 0.55 mmol) in anhydrous dimethylformamide (10 cm³) under a nitrogen atmosphere and the mixture was heated to 60° C. A solution of Intermediate 3 [(0.10 g) in anhydrous dimethylformamide (10 cm³)] was added dropwise over a period of 2 h and the mixture stirred for a further 36 h at 60° C. The cooled reaction mixture was filtered and solvent removed under reduced pressure to give a pale yellow oil. Purification was afforded by preparative HPLC SYNCHROPAK® CM300 cation exchange), to afford the title compound (0.03 g) as a colourless oil.

HPLC tR 6.8 min observed at λ=254 nm SYNCHROPAK® CM300 cation exchange) with gradient elution, 1.4 ml min⁻1, A—H₂O, B=1.0M—NH₄OAc, C=MeCN; from t=0 min, 80% A, 0% B. 20% C, to t=5 min, 60% A, 20% B, 20% C, to t=10 min. 0% A, 80% B, 20% C;

δ$_H$ (400 MHz, CDCl₃) 1.56 (3H, t, J 6.8 Hz, POCH₂C$\underline{H}_3$), 2.26–2.27 (2H, m, PCH₂C$\underline{H}_2$), 2.88–3.18 (14H, mult, $\overline{CH_2N+CH_2PO}$) 3.22 δ 3.25 (2H, ddd, J, 5.2 Hz, NCH₂PO) 3.75 δ 3.88 (1H—1H, ddt, J 6.4 Hz, CH₂NHCO₂PO), 4.33 (2H, d,quart, J 7.2 Hz, P.O.C$\underline{H}_2$CH₃), 5.49 br (2H, s, 2×N$\underline{H}$ CH₂CH₂N$\underline{H}$), 7.65–7.71 ($\overline{3H}$, m, aromatic C₆H₂$\underline{H}_3$), 8.24–8.27 (2H, m, aromatic C₆H₃$\underline{H}_2$) and 9.05 (1H, br, t, J 6 Hz (N$\underline{H}$COPh), m/z (DCI, NH₃) 398 (M⁺+2), 39⁻ (M⁺+1), 256, 142.

INTERMEDIATE 8

Preparation of a compound of formula (1b) where R¹ is —CH₃P(O)(OEt)(CH₂)₃NHCOPh and R² and R³ is each —CH₂P(O)(OEt)CH₃

To a stirred solution of Intermediate 7 (0.03 g) in dry tetrahydrofuran (20 cm³) was added the CH₃P(OEt) (0.03 g) followed by formaldehyde (0.01 g) under an atmosphere of dry N₂. The resulting mixture was refluxed for 16 h with soxhlet drying using freshly activated 4A molecular sieves. After cooling the mixture was filtered and the tetrahydrofuan removed under reduced pressure to give a pale yellow oil. The crude title ester was purified via alumina chromatography 13% MeOH in CH₂Cl₂ as eluant) to yield the ester (0.025 g) as a colourless oil. HPLC tR 5.1 min observed at λ=254 mm. (SYNCHROPAK® CM300 cation exchange) with gradient elution, 1.4 ml min⁻¹, A=H₂O, B=1.0M NH₄OAc, C=MeCN; from t=0 min. 80%A. 0% B, 20% C, to t=5 min. 60% A, 20% B, 20% C, to t=10 min, 0% A, 80% B, 20% C;

δ$_H$ (250 MHz, CDCl₃) inter alia 1.26 (15H, mult, PMe+ OCH₂C$\underline{H}_3$) 1.98 (4H, br, mult, PCH₂+PCH₂CH₂) 2.62–2.91 (18 H, m together 3×P.CH₂N and Ring (CH₂s), 3.48–3.75 (2H, mult, broad, C$\underline{\tilde{N}}$HCO), 3.97–4.27 (6H, m. together 3×P.O. CH₂Me), 7.41–7.49 (3H, m, aromatic C₆H₂H) and 8.05 br (1H, s, N$\underline{H}$COPh), m/z (DCl, NH₃) 638 (M⁺+2), 637 (M⁺+1) 545, 256 and 109.

INTERMEDIATE 9

Preparation of the hydrochloride salt of a salt of a compound of formula (1b) where R¹ is —CH₂P(O)(OH)(CH₂)₃NH₂ and R² and R³ is each —CH₂P(O)(OH)CH₃

A solution of Intermediate 8 (0.02 g) in 6M —HCl (10 cm³) was heated at 140° C. for 48 hours to afford complete hydrolysis (as seen by Hnmr). The cooled solution was washed firstly with CH₂Cl₂ (2x) and than diethyl ether (2x) before evaporation under reduced pressure to give the title hydrochloride as a glassy foam (0.011 g).

δ$_H$ (D₂O) 1.36–1.50 (6H, mult of doublets, P—CH₃), 17.75–1.85 (4H, mult, CH₂PO+CH₂CH₂PO), 3.01 (2H, mult, CH₂NH₃+) 3.10–3.50 (18H, $\overline{CH_2N+PCH_2N}$, mult) m/z (f.a.b., glyerol) 449 (M⁺+1). 44 S (M+)

INTERMEDIATE 10

Preparation of a compound of formula (1b) where R1 is

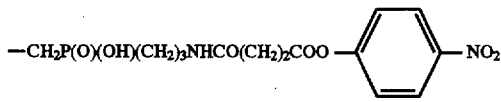

—CH₂P(O)(OH)(CH₂)₃NHCO(CH₂)₂COO—〈 〉—NO₂ and R² and R³ is each —CH₂P(O)(OH)CH₃

The title nitrophenyl ester was prepared using Intermediate 9 and the di-4-nitrophenyl ester succinic acid as described for the preparation of Intermediate 6

INTERMEDIATES 11 and 12

Preparation of the ⁹⁰Y complexes of Intermediate 6 and 10

To a solution of either Intermediate 6 (5μ∂m³) or Intermediate 10 (5μ∂m²) in tetramethylammonium morpholinoethanesulphate (MES) buffer (0.1M, pH, 6.8, 90μ∂m³) at 37° C. was added 5μCi of ⁹⁰Y (5μ∂m³ of an aqueous solution of the trichloride) to produce the labelled products Intermediates 11 and 12. After 0.5 h each mixture containing either Intermediate 11 or 12 was analysed by HPLC (AX 300: 0.2M NH₄OAc: 10% CH₃CN) with radiometric detection (LKB radiation detector) following quenching of the labelling reaction by addition of a 500 fold excess of diethylenetriaminepentaacetic acid (DTPA). Radiolabelling yields of 82% were determined (hplc radiometry integrating the ⁹⁰Y-ligand peak (4.5 mins) against ⁹⁰Y-DTPA (15 mins). After maintaining the complex at this pH at 298K in the presence of a 500 fold excess of DTPA, no change in the relative concentration of complex was deserved at 24, and 72 h.

EXAMPLE

The labelled products, Intermediates 11 and 12 were each coupled to the antibody B72.3 using the following procedure.

B72.3 monoclonal antibody [Colcher, D. et al Proc. Nat. Acad. Sci, USA (1981), 78, 3199; 3.75 mg previously modified with Traut's reagent] in 0.1M phosphate buffer (containing 2 mM ethylenediaminetetraacetic acid; pH 8.0; 110 μl) was added to either Intermediate 11 or 12 (25 μl) and the mixture was incubated at 37° C. for 90 minutes then purified by PD-10 gel filtration chromatography to yield the desired labelled conjugate products.

We claim:

1. A compound selected from the group consisting of (i) a conjugate of a polypeptide bound to a group of the formula:

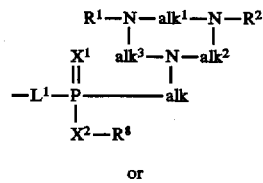

or

-continued $$\begin{array}{c} R^1-N-alk^1-N-R^2 \\ | \quad\quad\quad | \\ alk^4 \quad\quad alk^2 \\ | \quad\quad\quad | \\ X^1 \quad N-alk^3-N-R^3 \\ \| \quad | \\ -L^1-P-alk \\ | \\ X^2-R^8 \end{array}$$

in which the polypeptide is bound to said group through $L^1$ and each of $alk^1$, $alk^2$, $alk^3$, and $alk^4$, independently of the other, is alkylene of 1 to 4 carbon atoms, unsubstituted or substituted with alkyl of 1 to 6 carbon atoms;

each of $R^1$, $R^2$, and $R^3$, independently of the other, is hydrogen or —alk—$R^5$;

alk is straight or branched alkylene of 1 to 6 carbon atoms;

$R^5$ is hydrogen, $$-\overset{X^1}{\underset{\|}{P}}(-X^2R^8)_L,\ -COOH,\ or\ -CON\overset{R^6}{\underset{R^7}{\diagdown}}\ ;$$

L is selected from the group consisting of a linking group $L^1$, alkyl of from 1 to 10 carbon atoms, alkenyl of from 2 to 10 carbon atoms, alkynyl of from 2 to 10 carbon atoms, alkoxy of from 1 to 10 carbon atoms, alkylthio of from 1 to 10 carbon atoms, cycloalkyl of from 3 to 8 carbon atoms, cycloalkenyl of from 4 to 8 carbon atoms, aryl of from 6 to 12 carbon atoms, aralkyl of from 6 to 12 aryl and 1 to 6 alkyl carbon atoms, heteroaryl of from 4 to 10 carbon atoms and heteroaralkyl of from 4 to 10 heteroaryl and 1 to 6 alkyl carbon atoms;

said alkyl, alkenyl, alkynyl, alkoxy or alkylthio group being uninterrupted or interrupted with one or more members selected from the group consisting of —O—, —S— and —N($R^9$)—;

said alkyl, alkoxy, aryl, aralkyl, heteroaryl or heteroaralkyl group being unsubstituted or substituted with one or more members selected from the group consisting of halo, hydroxy, alkyl of from 1 to 6 carbon atoms, alkoxy of from 1 to 6 carbon atoms, alkylthio of from 1 to 6 carbon atoms, —NR$^{10}$R$^{11}$, nitro, cyano, carboxyl, —CONR$^{12}$R$^{13}$, —SO$_2$NR$^{12}$R$^{13}$ and cycloalkyl of from 3 to 8 carbon atoms;

each of $X^1$ and $X^2$, independently of the other, is oxygen or sulfur;

$L^1$ is a linking group selected from the group consisting of alkylene of from 1 to 10 carbon atoms, alkenylene of from 2 to 10 carbon atoms, and alkynylene of from 2 to 10 carbon atoms which alkylene, alkenylene, or alkynylene is uninterrupted or interrupted with one or more members selected from the group consisting of —O—, —S—, —N($R^9$)—, —CON($R^9$)—, or —N($R^9$)CO—, a cycloalkane ring of 3 to 8 carbon atoms, an aromatic ring of 6 to 12 carbon atoms, or a pyridine, furane, or thiophene ring, said linking group being unsubstituted or substituted with one or more members selected from the group consisting of halo, alkyl of 1 to 6 carbon atoms, alkoxy of 1 to 6 carbon atoms, hydroxy, nitro $$-N\overset{R^{10}}{\underset{R^{11}}{\diagdown}}, \text{ and } -(CH_2)_d\overset{O}{\underset{\|}{C}}N\overset{R^{12}}{\underset{R^{13}}{\diagdown}}\ ;$$

each of $R^6$, $R^7$, $R^8$, $R^9$, $R^{10}$, and $R^{12}$, independently of the other, is hydrogen or alkyl of 1 to 6 carbon atoms;
each of $R^{11}$ and $R^{13}$, independently of the other, is alkyl of 1 to 6 carbon atoms; and
d has a value of from 0 to 4;

(ii) a complex of said conjugate with a di- or tripositive metal; and (iii) a salt of said conjugate or said complex.

2. A compound according to claim 1 having the formula:

$$\begin{array}{c} R^1-N-alk^1-N-R^2 \\ | \quad\quad\quad | \\ alk^3-N-alk^2 \\ | \\ X^1 \\ \| \\ -L^1-P-\!\!-\!\!-alk \\ | \\ X^2-R^9 \end{array}$$

wherein each of $alk^1$, $alk^2$, and $alk^3$, and independently of the other, is alkylene of 1 to 4 carbon atoms and each of $X^1$ and $X^2$ is oxygen.

3. A compound according to claim 2 wherein each of $alk^1$, $alk^2$, and $alk^3$ is —CH$_2$CH$_2$—.

4. A compound according to claim 3 wherein each of $R^1$ and $R^2$, independently of the other, is hydrogen or $$-CH_2-\overset{O}{\underset{\|}{P}}-O-R^8.$$

5. A compound according to claim 3 which is a complex of said conjugate with indium, yttrium, or gadolinium.

6. A compound according to claim 1 having the formula:

$$\begin{array}{c} R^1-N-alk^1-N-R^2 \\ | \quad\quad\quad | \\ alk^4 \quad\quad alk^2 \\ | \quad\quad\quad | \\ X^1 \quad N-alk^3-N-R^3 \\ \| \quad | \\ -L^1-P-\!\!-\!\!-\!\!-alk \\ | \\ X^2-R^8 \end{array}$$

wherein each of $alk^1$, $alk^2$, $alk^3$, and $alk^4$, independently of the other, is alkylene of 1 to 4 carbon atoms and each of $X^1$ and $X^2$ is oxygen.

7. A compound according to claim 6 wherein each of $alk^1$, $alk^2$, $alk^3$ and $alk^4$ is —CH$_2$CH$_2$—.

8. A compound according to claim 7 wherein each of $R^1$, $R^2$, and $R^3$, independently of the other, is hydrogen or $$-CH_2-\overset{O}{\underset{\|}{P}}(-O-R^8)_L.$$

9. A compound according to claim 7 which is a complex of said conjugate with yttrium or gadolinium.

* * * * *